United States Patent [19]

Soldner et al.

[11] 4,047,520
[45] Sept. 13, 1977

[54] ULTRASONIC IMAGING APPARATUS OPERATING ACCORDING TO THE IMPULSE-ECHO TECHNIQUE

[75] Inventors: Richard Ernst Soldner, Erlangen; Rudolf Rattmann, Herzogenaurach, both of Germany

[73] Assignee: Siemens Aktiengesellschaft, Berlin & Munich, Germany

[21] Appl. No.: 702,589

[22] Filed: July 6, 1976

[30] Foreign Application Priority Data

Aug. 5, 1975 Germany .............................. 2534974

[51] Int. Cl.² ............................................. A61B 10/00
[52] U.S. Cl. ................................... 128/2 V; 73/67.8 S
[58] Field of Search .......................... 128/2 V, 2.05 Z; 73/67.8 R, 67.8 S

[56] References Cited
U.S. PATENT DOCUMENTS 3,470,868  10/1969  Krause et al. ....................... 128/2 V Primary Examiner—Robert W. Michell
Assistant Examiner—Michael H. Thaler
Attorney, Agent, or Firm—Hill, Gross, Simpson, Van Santen, Steadman, Chiara & Simpson

[57] ABSTRACT

An ultrasonic applicator including a parabolic reflector for reflecting ultrasonic beam energy for ultrasonic sectional scanning particularly for medical diagnostic purposes, has its image registering system compensated for the variable sweep velocity of the ultrasonic beam energy within the body region under examination by the provision of a rotary mark carrier with a series of angularly offset marks of variable spacing such that as the mark carrier rotates at a constant rate in synchronism with the rotary ultrasonic transducer head, the marks are scanned at a relatively rapid rate as the ultrasonic impulses are reflected at the border regions of the parabola and are scanned at a progressively slower rate during transducing via points progressively closer to the central region of the parabola.

14 Claims, 7 Drawing Figures

ULTRASONIC IMAGING APPARATUS OPERATING ACCORDING TO THE IMPULSE-ECHO TECHNIQUE

BACKGROUND OF THE INVENTION

This invention concerns an ultrasonic imaging apparatus operating according to the impulse-echo technique, particularly for medical diagnosis, with an ultrasonic applicator for the linear ultrasonic scanning of a body region and an image registering device with a line generator for the formation of the echo impulses as an image line and an image generator for the displacement of successive image lines in dependence upon the displacement of the ultrasonic beam in the object, wherein the ultrasonic applicator comprises a parabolic reflector and an ultrasonic transducer head arranged for rotation about the focal line of the parabolic reflector, the head having a plurality of ultrasonic transducers which are to be focused on the reflector and which function as transmitters and/or receivers, and wherein an angle of rotation responsive signal generator is assigned to said transducers and in dependence upon the angular movement of the respective active transducer, supplies to the image generator an image line displacement voltage for displacing the successive image lines which initially has a relatively rapid rate of increase, which increases at a slower rate as the active transducer traverses a central region of the reflector, and again provides a more rapid rate of increase toward the end of a traverse of the reflector, in conformity to the variable displacement velocities of the reflected ultrasonic beam at the reflector border zones in comparison to the reflector center zone.

An ultrasonic imaging device with an ultrasonic applicator is prior art from U.S. Pat. No 3,470,868, which exhibits a cylindrical parabolic reflector, in whose focal line is disposed an ultrasonic transmitting/receiving head (with a total of two transmitting/receiving transducers) the head being arranged rotatably about the focal line as axis, and being adjustable along the focal line. During rapid rotation of the ultrasonic head about the focal line, an ultrasonic beam radiated in the direction of the reflector and reflected from the latter into a body which is to be examined, for example, is displaced parallel to itself in the body area, on account of the reflection properties of the reflector. Thus, the reflected ultrasonic beam scans this body area along a rapid succession of lines which are parallel to one another. During the corresponding linear image formation of the echo signals received from a scanning line in the body area, respectively, on a viewing screen of an oscilloscope as the display and/or recording device, a sectional view of the body region to be examined is obtained in the scanning plane. Planes parallel thereto are obtained by means of a corresponding displacement of the ultrasonic transmitting receiving head in the direction along the focal line of the parabolic reflector. However, the prior art ultrasonic imaging device has the following disadvantage. If the rotation of the rotary shaft for the ultrasonic head (employing an electric motor as the rotary drive, for example) takes place with uniform angular velocity, the beam of the respective presently active ultrasonic transmitter/receiver which is reflected by the reflector moves perpendicular to its direction of propagation in the border zones of the parabola with greater velocity (perpendicular to the direction of the parallel-proceeding sound waves) than in the central zone of the parabola. The consequence of this is that the scanning of the area under investigation does not proceed with equal velocity; thus the information density from this area is not uniform, on the one hand, and non-linear distortions occur during image registration on the other hand. Attempts have already been undertaken in order to eliminate these disadvantages at least partially. Thus, for example, in the devices according to U.S. Pat. No. 3,470,868, angle of rotation responsive signal generators have been introduced which at least provide a line displacement voltage at the image generator having the initially described variable rate of rise characteristic for the purpose of correction of non-linear distortions during image registration. However, the modulation of the image line displacement voltage took place by means of an inductive impedance change using a pair of cam plates, which in dependence upon the angular position of the respective assigned ultrasonic transducer, penetrated more or less deeply in the air gap of a high frequency generator. Angle of rotation responsive signal generators of this type are not only extremely complicated and costly from a technical point of view; in addition, accurate reproduction thereof is difficult leading to relatively high manufacturing costs. Moreover, the linearization effect is not optimal on account of the poor reproducibility of the angle responsive generator, and in addition, non-uniform information densities result. The U.S. Pat. No. 3,470,868 describes additional attempts at a solution. However, the paths of solution initiated therein are entirely of a mechanical type; that is, compensation for the non-linear effects, or the non-uniform information densities, respectively, takes place by means of engagement into the drive train of the rotary drive of the ultrasonic head in such a manner that, by means of correspondingly designed cam plates, the original drive with uniform angular velocity is converted into a drive with non-uniform velocity (such that the speed of rotation of the sound head in the region of the border zones of the reflector is slower than in the central one of the reflector). These purely mechanical solutions are also technically too complicated and likewise, as practice has shown, do not compensate for nonlinearities or variable information densities from the area under investigation to the high degree which is actually desirable.

SUMMARY OF THE INVENTION

It is an object of the present invention to construct an ultrasonic imaging device of the type initially referred to such that, with solution means which are technically much less complicated and which at the same time are capable of greatly improved accuracy of reproduction, optimal conditions of linearity are insured on the one hand, and if required, extremely constant information densities are also attainable on the other hand.

As specified by the invention, the problem is solved in that the angle of rotation responsive signal generator comprises a marking system consisting of angle of rotation marks, assigned to the ultrasonic transitting/receiving transducers, the marking system rotating with the transducers and the number of marks being selected to correspond to the desired angular resolution accuracy for the respective transmitting/receiving transducers, and the distances between the marks being wider corresponding to the lower ultrasonic scanning velocity for a given angular increment of rotation of the transducers at the reflector mid region and being narrower corresponding to the higher ultrasonic scanning velocity for corresponding angular increments of rotation with respect to the region of the reflector edges, the marking system further comprising a mark scanner for scanning of the marks during rotation thereof with the transducers and for controlling the rate of image line displacement in dependence upon the rate of scanning of the individually scanned marks, such that the image line displacement takes place rapidly during scanning of a rapid succession of marks, and takes place correspondingly less rapidly during scanning of a less rapid succession of marks.

In contrast to an inductive angle responsive device using cam plates, an angle of rotation responsive signal generator consisting of angle of rotation marks as well as a mark scanner can be more easily constructed and also can be reproduced accurately in mass production. This not only simplifies the technical expenditure; an optimal linearity during image synthesis also results, and with a corresponding adaptation of the ultrasonic impulse repetition rate to the rate of mark scanning by the mark scanner, for example, an extremely uniform information density in the ultrasonic image additionally results.

Other objects, features and advantages of the present invention will be apparent from the following detailed description of an exemplary embodiment, taken in connection with the accompanying drawings.

DETAILED DESCRIPTION

Figures 1, 2:
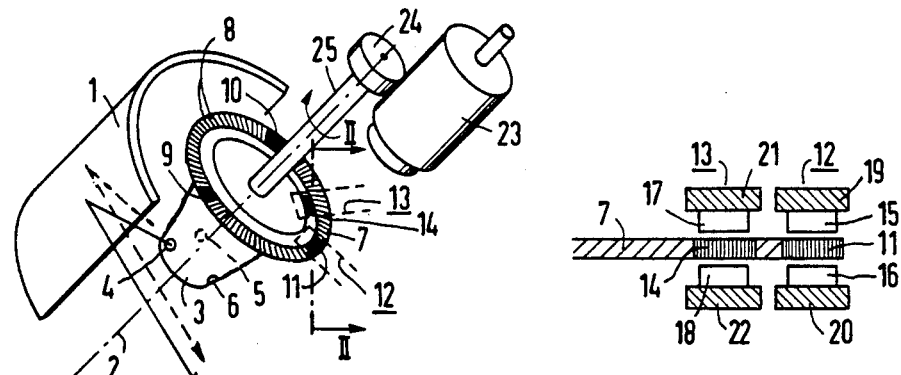
FIG. 1 is a schematic perspective illustration of an ultrasonic applicator incorporating an ultrasonic imaging system according to the present invention.
FIG. 2 is a fragmentary sectional view taken along the line II—II of FIG. 1 and shows an optoelectric mark scanner system cooperating with a rotary mark carrier, and which together form a component part of the angle of rotation responsive signal generator for the ultrasonic imaging system according to the present invention.

In FIG. 1, reference numeral 1 designates a cylindrical parabolic reflector, in whose focal line 2 an ultrasonic head section 3 is arranged for rotation about the focal line as axis and for longitudinal adjustment along the focal line. The ultrasonic head assembly of FIG. 1 has altogether three ultrasonic transducers 4, 5 and 6, which are arranged about the circumference of the lower head section 3, at angular separations of 120°. Of transducers 4 through 6, only transducers 4 and 6 are visible in the perspective illustration of FIG. 1. However, the actually non-visible third transducer 5 is indicated in dotted outline. Individual transducers 4 through 6, in the activated state, respectively, produce an ultrasonic beam consisting of ultrasonic impulses which are transmitted toward successive points along reflector 1, and which are reflected by the latter, via a non-illustrated water coupling path, for example, into an object which is to be examined. During rapid rotation of ultrasonic head 3, the ultrasonic beam of the respective activated ultrasonic transducer 4, 5 or 6, scans the object along mutually parallel lines, due to the reflection properties of the reflector 1. The echo impulses originating from each ultrasonic scanning line, which are received by the presently active ultrasonic transducer operating as both transmitter and receiver, are finally registered in corresponding linear form on the viewing screen of an oscilloscope tube. Thus, the desired ultrasonic echo sectional view of the object results.

Figure 7:
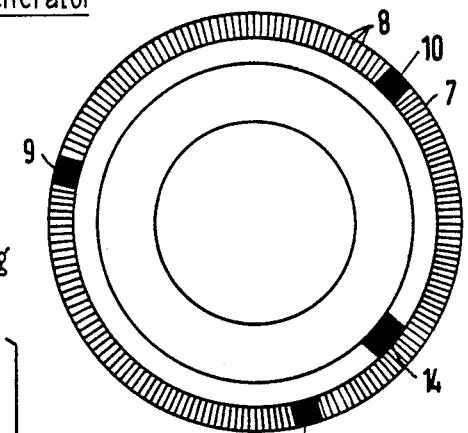
FIG. 7 is a diagrammatic illustration of a practical exemplary embodiment of the mark carrier for an ultrasonic imaging system in accordance with the present invention.

In the present exemplary embodiment, an incremental angle-disk or mark carrier in combination with two optoelectric impulse generators, functions as a significant component part of the angle of rotation responsive signal generator, and simultaneously functions as a control element for the chronologically synchronous switching on-or off of the individual transducers as transmitter and receiver. In FIG. 1, the angle-disk 7 is arranged at the upper side of the ultrasonic head section 3. The disk, which consists of a translucent base material, preferably plexiglas, for example, exhibits on its circumference a plurality of thin black radially directed lines 8 arranged in three angle-sectors of 120° each with intervening heavier black control areas 9, 10 and 11. The angular relationship of disk 7 to ultrasonic transducers 4 through 6 can be such that black segment 9 is located directly above transducer 4, black segment 10 directly above transducer 5, and black segment 11 directly above transducer 6. Black segments or opaque control marks 9, 10 and 11 primarily serve the purpose of marking the beginning of each transmitting/receiving period, respectively, of one of the ultrasonic transducers 4 through 6. The thin black lines 8, on the other hand, mark respective angular increments of movement of the assigned ultrasonic transducer 4, 5 or 6, respectively, in the course of the respective transmitting-/receiving interval of the assigned transducer, which angular increments on the whole are to correspond to constantly uniform displacement steps of the ultrasonic scanning beam in the body region under examination. The spacing between the individual lines 8 in each of the three 120° angle sectors which are separated by the respective black segments 9 through 11, is accordingly variable selected such that the line spacing becomes increasingly narrower near each black segment 9, 10, 11, relative to the line spacing in the center portions intermediate such black segments. In the exemplary embodiment according to FIG. 7, for example, each sector between pairs of the black segments 9 through 11 contains approximately 160 thin individual lines, the line spacing in each sector central portion being equal to approximately eight-tenths of a millimeter (0.8 mm), and decreasing continuously in both directions toward the respective adjoining black segments 9–11 to a spacing of approximately five-tenths of a millimeter (0.5 mm). A first optoelectric generator 12 is constructed to be actuated by light interruptions, and serves the purpose of scanning the line segments or marks 8 as well as the black segments or control marks 9 through 11. A second optoelectric generator 13 is likewise constructed to respond to light interruptions and functions in combination with an additional thick black segment 14 on the angle disk 7 which as indicated in FIG. 7 is disposed nearer the center of the disk, the further control mark 14 serving as an additional synchronization element for the purpose of insuring chronologically correct activation of the respective ultrasonic transducers 4, 5 and 6. As is made clearer in the sectional view according to FIG. 2, each optoelectric generator 12 or 12, respectively, comprises a light producer which is to be preferably a light emitting diode in the present illustrated embodiment. A light receiver, for example a photo-conductive cell, is assigned to each of these light producers on the opposite side of the disk. In FIG. 2, the light producer of the optoelectric generator 12 is designated by 15 and the respective light receiver is designated by 16. The light producer of the photoelectric generator 13, in contrast, bears the identifying numeral 17, and the respective light receiver bears the identifying numeral 18. Elements 19 through 22 are support elements for the purpose of mounting the light producers and light receivers respectively of the optoelectric generators 12 and 13.

An electric motor 23 serves as the rotary drive element for the sound head 3 and the angle disk 7 of the applicator as shown in FIGS. 1 and 2, the motor 23 being operatively connected to rotary shaft 25 of sound head 3 via a friction drive or a gear drive 24, for example.

Figure 3:
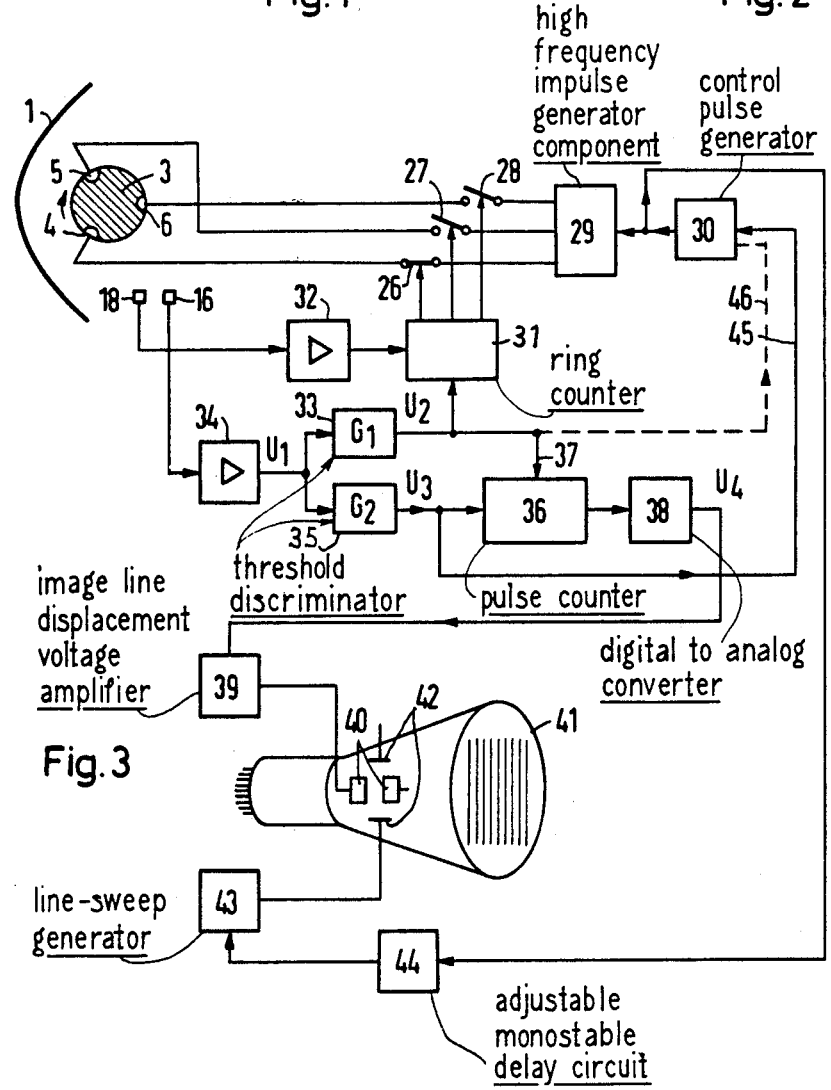
FIG. 3 illustrates a basic circuit diagram for the inventive ultrasonic sectional imaging system.

In FIG. 3, which illustrates the entire arrangement of the ultrasonic sectional imaging apparatus in basic construction, the reflector is again designated by reference numeral 1, the ultrasonic head by reference numeral 3, and the three ultrasonic transducers arranged at angles of 120° are designated by reference numerals 4, 5 and 6. The illustration corresponds to a cross-section of ultrasonic head 3 below the angle disk 7. In FIG. 3, of the optoelectric generator devices 12 and 13, only the respective assigned light receivers 16 and 18 are indicated. Ultrasonic transducers 4, 5 and 6 of the basic circuit diagram of FIG. 3 are each capable of being individually connected to a high frequency impulse generator of component 29 via a respective assigned electrically controlled switch 26, 27 or 28. The high frequency impulse generator of component 29 is controlled as to its impulse supply rate by the rate of control pulses supplied thereto by means of impulse generator 30. Switching on of the switches 26, 27 or 28 according to the required schedule takes place via the switching impulse outputs of a ring counter 31. The ring counter 31 is provided with two control inputs the first of which is connected to the light receiver 18 of the optoelectric generator 13 via a signal amplifier 32. The second control input is connected to the output of a first threshold discriminator 33 which receives the electric pulse signals emitted by light receiver 16 as a function of light interruptions at the optoelectric generator 12 as amplified in amplifier 34. In addition, reference numeral 35 designates a second threshold discriminator for the signals from amplifier 34 and this second discriminator is connected at its output side to the counter input of a pulse counter 36. The pulse counter 36 has a switching input 37 connected with the output of the first threshold discriminator 33 which serves to reset the counter 36 to an initial count condition. The counter 36 controls a digital to analog converter 38, and the analog output of converter 38 is supplied to an amplifier 39 which in turn is connected to a pair of horizontal deflection plates 40 of an electron beam tube 41 for the purpose of successively deflecting the electron beam to trace successive image lines as diagrammatically indicated on the face of the tube 41 in FIG. 3. A pair of vertical deflection plates 42 of tube 41, on the other hand, is connected to a line-sweep generator 43 and the latter is in turn connected to the output of control pulse generator 30 in order to control the initiation of successive image line deflection cycles in dependence upon the initiation of successive impulse transmission times of the successive ultrasonic energy impulses to be transmitted by the active transducer. In order to take into consideration preliminary time intervals, for example the ultrasonic transmitting-/receiving impulse transmission time in a preliminary water path, an adjustable monostable delay circuit 44 may, if necessary, for example, be placed in a circuit between the control pulse generator 30 and the line-sweep generator 43. The delay circuit 44 may be adjusted so as to provide a delay of a predetermined period of time between the transmitting time for a given ultrasonic beam impulse and the initiation of a line-sweep operation for the purpose of registering the associated echo impulses. Line 45 leading to the control pulse generator 30, or the additional line 46 shown as a dash line in FIG. 3, are control lines for the purpose of controlling the initiation of each control pulse and thus control the pulse frequency of the impulse generator 30, the control line 45 serving to control the rate of control pulse generation in dependence upon the output of the second discriminator 35, and the control line 46 optionally controlling the rate of control pulse generation by component 30 in dependence upon the output of the first discriminator 33. Of course, the control pulse generator 30 may be a free running multivibrator circuit with an adjusted desired output pulse rate if control of the control pulse rate from the mark scanner is considered unnecessary for a particular use of the illustrated embodiment.

Figure 4:
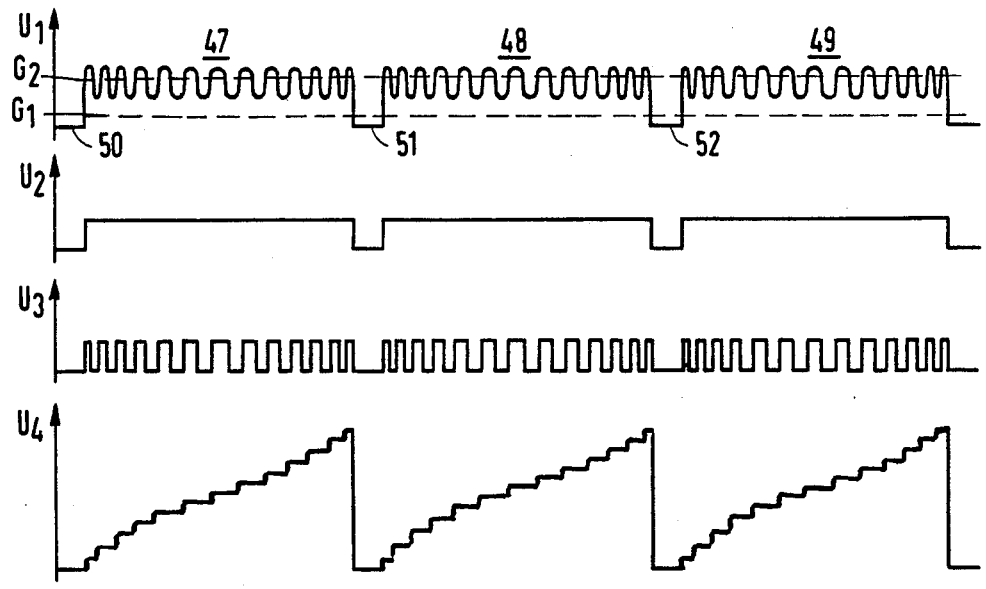
FIG. 4 constitutes a diagram showing the waveform as a function of time of the most important signals occurring in the basic circuit according to FIG. 3.

The mode of operation of the imaging device according to FIG. 3 will be apparent in connection with FIGS. 1 and 2, as well as when considered with the voltage waveforms shown in FIG. 4. The following description will correlate the waveforms of FIG. 4 with the structure of FIGS. 1–3.

By energizing motor 23, FIG. 1, ultrasonic head 3 together with angle disk 7 is driven at a rapid rotational rate. The rotation of the angle disk 7 in turn has the effect that the light beam of the optoelectric generator 12 is periodically interrupted at the mark scanning rate corresponding to the variable spacing of the opaque lines 8. Thus, the mark signals from generator 12 after amplification in amplifier 34 produce a voltage signal $U_1(t)$ which has a waveform as a function of time as schematically illustrated at $U_1$ in FIG. 4. In FIG. 3, amplifier 34 is shown as being connected with the output of light receiver 16 and as supplying at its output the waveform diagrammatically indicated at $U_1$ in FIG. 4. The voltage waveform $U_1$ of FIG. 4 is repeated for each revolution of the sound head 3 and the angle disk 7, respectively, and is essentially characterized by a total of three successive trains 47, 48 and 49 of mark impulses of relatively brief duration which are interrupted by longer pulse pauses or control intervals 50, 51 and 52. The longer duration interruption signals or control intervals 50, 51 and 52 originate respectively from the light-interruptions by the opaque control segments 9, 10 and 11 on disk 7. The impulse trains of the brief duration mark impulses are designated by reference numerals 47, 48 and 49 in FIG. 4 and are the result of the light interruptions produced by scanning of the narrow lines 8 of respective 120° segments on the angle disk 7. Since, as previously mentioned, the line spacing in the three 120° segments decreases from a central portion toward the respective adjacent wider black segments 9-11, the mark impulses near the beginning or end of the respective trains 47, 48 and 49 of shorter overall duration and thus occur at shorter intervals than the impulses occurring in the central portions of the impulse trains. The voltage $U_1(t)$ supplied by amplifier 34 is simultaneously supplied to the first and second threshold discriminators 33 and 35. In accordance with the threshold value indicated by dash line $G_1$ in FIG. 4, the threshold discriminator 33 operates as a clipper and limits its response to the waveform $U_1$ of FIG. 4 to values up to the threshold $G_1$. Thus, a voltage signal $U_2(t)$ results at the output of threshold discriminator 33 having a waveform as indicated at $U_2$ in FIG. 4. The threshold discriminator 35 operates with a minimum amplitude threshold as indicated by the dash line $G_2$ in FIG. 4 and transmits only voltages which exceed this threshold. Thus, a voltage signal $U_3(t)$ results as represented by the waveform $U_3$ of FIG. 4 at the output of threshold discriminator 35. The individual impulses of the input impulse trains 47, 48 and 49 in FIG. 4 (for example the positive-going transitions of waveform $U_3$) are then counted in a digital counter 36 which may operate as a binary counter, for example. The counter stages of counter 36 may be coupled to respect the stages of the digital to analog converter 38 so as to generate an analog image deflection voltage corresponding to the condition of the respective stages of the counter 36. Thus, the output of the converter 38 exhibits the stepped voltage change of a voltage $U_4(t)$ as indicated at $U_4$ in FIG. 4. The periodic resetting of counter 36 to its zero count condition at the end of each counting interval takes place each time with the scanning of a black control segment 9, 10 or 11, as sensed by the corresponding light interruption at the optoelectric generator 12. Since this coincides with the trailing (negative-going) edge of the waveform $U_2$ of FIG. 4, the signal $U_2(t)$ also serves as a triggering impulse for the purpose of resetting counter 36 via control line 37.

From the waveform as a function of time of the image line displacement signal $U_4(t)$ as indicated at $U_4$ in FIG. 4, an image line displacement results on the viewing screen of tube 41 such that the successive image lines are at least approximately all equally spaced as diagrammatically indicated in FIG. 3. In order to provide such substantially equal spacing of the image lines with a constant rate of rotation of the ultrasonic transducers, the rate of image line displacement is relatively rapid at the beginning of an image generating cycle, gradually becomes slower toward the center of the image, and, after crossing the center of the image, correspondingly increases to a relatively rapid rate again toward the end of the image generating cycle. However, this variable image line displacement corresponds to the variation in the ultrasonic scanning velocity within the body region being examined which as described increases as a function of distance from the central zone of the reflector outwardly toward the border zones of the reflector. Thus, the desired linearization effect results in the image representation, and with a corresponding adaptation of the ultrasonic impulse rate by means of a control line such as 45, a good constant information density also results, which small be explained in greater detail in the following. The described mode of operation solely concerns the production of an image deflection of voltage according to the waveform $U_4$ of FIG. 4. What is still lacking is the direct chronological synchronization between the transmitting-or-receiving-times of each transducer 4, 5, 6 with the image line displacement signal $U_4(t)$ as represented by waveform $U_4$ in FIG. 4. In combining both optoelectric generators 12 and 13 with ring counter 31, as well as with switches 26 through 28, this synchronization results for the switching on of the individual transducers 4 through 6, as follows.

In the illustration according to FIG. 1, the light beam of the optoelectric generator 12 impinges on the opaque control mark 11 simultaneously with the impingement of the light beam of the optoelectric generator 13 onto the further opaque control mark 14. As shown in FIG. 1, at this time, transducer 4 which is below the black mark 9 is positioned directly at the entry region of reflector 1. The simultaneous arrival of the control marks 11 and 14 at the mark scanner means has the effect of producing simultaneous interruption impulses at the output of amplifier 32 and at the output of the threshold discriminator 33. The simultaneous arrival of these interruptions and impulses, specifically, in turn, brings about an impulse emission in the ring counter 31 to insure that the ring counter is set to the condition such that switch 26 is closed and transducer 4 activated for the purpose of radiation and reception of ultrasonic signals in association with the impulse generator component 29. The successive interruptions of the light beam of the optoelectric generator 12 by means of the opaque control segments 10 and 9 (for the illustrated direction of rotation of sound head 3) then successively step the ring counter 31 to a second condition where switch 28 is closed and switches 26 and 27 are kept open, and then to a third condition where switch 27 is closed while switches 26 and 28 are kept open. Thus, in the successive first second and third conditions of ring counter 31, first transducer 4, then transducer 6, and finally transducer 5 are activated in synchronism with the rotary movement of the head assembly. This process is repeated periodically with each revolution of the ultrasonic head 3 and correct synchronism is insured by the renewed coincidence of the interruption impulses produced by control marks 11 and 14 in each such revolution.

Figure 5:
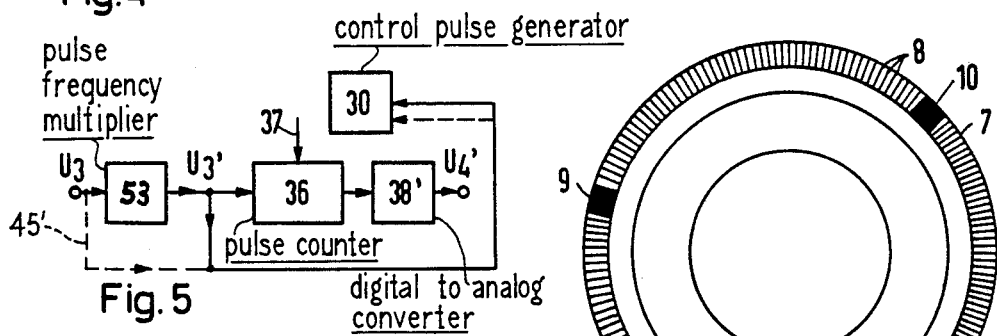
FIGS. 5 and 6 illustrate modifications of the basic circuit of FIG. 3.

In the exemplary embodiment according to FIG. 3, there are various possibilities regarding the selection of the image line displacement frequency. Since, as stipulated, each impulse of the optoelectric generator 12 corresponds to a step of the deflection beam (in the horizontal direction as viewed in FIG. 3) on the image tube 41 by a substantially constant value, the number of impulses on each of the trains 47, 48 and 49 in FIG. 4 may now be selected so as to be equal to the number of desired image lines to be produced on the registration device 41. With this selection, the impulse sequence $U_3(t)$ at the output of the threshold discriminator 35 may be utilized directly for the purpose of triggering the control pulse generator 30 for the emission of corresponding trigger pulses for actuating the high frequency generator 29, such that the impulses from the component 29 are directly synchronized with the pulses of the waveform $U_3$ of FIG. 4. In this case, a number of lines results which corresponds to the number of lines on the angle disk 7 between two successive opaque control segments, the resulting image lines on the registration device such as indicative at 41 having a line spacing which is always exactly constant, and thus also having a constant information density, independent of any fluctuations in the drive system for the transducer head 3 whatsoever. It is just as possible, however, to synchronize the control pulses from the impulse generator 30 only with the impulses of the impulse sequence $U_2(t)$ (for example, via the control line 46 indicated by dash lines in FIG. 3), and otherwise to permit the control pulse generator 30 to run freely with a preselectable repetition frequency. In this case, for example, the light interruption intervals of the waveform $U_2$ could be utilized to block the transmission of ultrasonic pulses from component 29 during the image retrace interval of the registration device such as 41, the higher amplitude levels of the waveform $U_2$ then corresponding to the transmission of a succession of control pulses from component 30 each operable to trigger an impule of high frequency energy from component 29. By way of example, the control pulse repetition frequency supplied by component 30 may be selected to correspond approximately to the foregoing line scanning frequency of optoelectric generator 12. The possibility also offers itself here that, by means of a corresponding frequency multiplication, for example by doubling the pulse waveform $U_3$ of FIG. 4 in a frequency doubling element 53 as shown in FIG. 5, the impulses of the impulse sequence $U_3(t)$ may be converted to a waveform $U'_3$ of twice the number of pulses of the waveform $U_3$ of FIG. 4. By such frequency multiplication, a waveform $U'_4$ can be produced with constant voltage steps, but with such voltage steps reduced to a fraction of the voltage steps represented for the waveform $U_4$ in FIG. 4. Such a reduction in the magnitude of the voltage steps for a waveform $U'_4$ correspondingly automatically leads to a decrease in the danger of a fluctuation between successive image line positions in the generation of an ultrasonic image.

Figure 6:
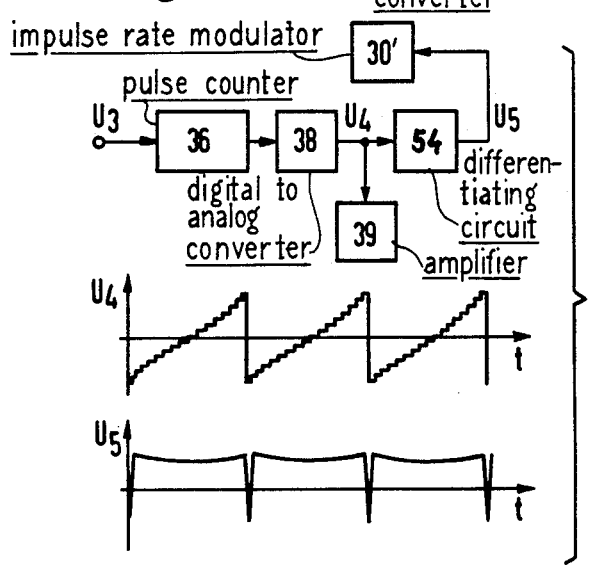

As a further modification, the control pulse sequence from the control generator 30, that is the transmission impulse sequence of the respective active ultrasonic transmitter, may be frequency modulated with a modulating voltage which is obtained, for example, by means of electrical differentiation of the image deflection voltage $U_4(t)$ as represented by waveform $U_4$ in FIG. 4. This possibility is indicated in the circuit modification according to FIG. 6, where the electrical differentiating element is designated by reference numeral 54 and is indicated as receiving a variable rate deflection voltage $U_4(t)$ having a waveform as indicated in the figure and which may be identical to the waveform $U_4$ of FIG. 4. From voltage $U_4(t$, a modulating voltage signal $U_5(t)$ results which may have a waveform $U_5$ as illustrated in FIG. 6. The voltage gradient $U_5(t)$ effects a frequency modulation of the pulse repetition frequency of control pulse generator 30' in such a manner that the control frequency is increased with increasing voltage $U_5(t)$ and is correspondingly decreased with a dropping of voltage amplitude of the voltage waveform $U_5$ of FIG. 6. By this means, specifically, particularly uniform information densities in the ultrasonic image result with a random ultrasonic scanning frequency.

In the exemplary embodiment of FIG. 1, the angle disk 7 is shown situated directly on the rotating ultrasonic head. However, it may of course also be arranged on a separate drive shaft, and may be located in a motor drive compartment which is sealed off from the compartment containing the ultrasonic transducers 4–6 and the parabolic reflector 1. Further, the angle disk 7 may have a separate drive shaft which is driven by the sound head shaft 25 with a one to three transmission ratio, for example (as a consequence of the use of a total of three ultrasonic transmitter/receiver elements staggered at 120° intervals). In such an instance, an angle disk is sufficient which exhibits only one single wide control mark segment for the purpose of marking the beginning of each marking pulse train, and in which the narrow lines, corresponding to the desired angular resolution, are not located within three sectors, but are distributed over the entire disk circumference which then rotates at three times the rate of the transducer head 3.

In addition, the exemplary embodiment preferbly operates with a total of three ultrasonic transducers, staggered at 120° intervals. Practice has demonstrated that optimal linearization conditions result hereby in connection with the invention, in view of the least possible expenditure of resources as well as the best image frequency conditions and image resolution conditions. The use of a number of transducer elements which is less than three or greater than three is, indeed, certainly provided within the framework of the invention. However, such embodiments involving a lesser number of transducers would impair the image quality, while embodiments with a greater number of transducers would increase the technical expenditure.

While there have been disclosed exemplary embodiments representing presently preferred practice of the claimed invention, it will be apparent that many modifications and variations may be effected without departing from the scope of the novel teachings and concepts of the present invention.

We claim as our invention:

1. In ultrasonic imaging apparatus operating according to the impulse-echo method, and including an ultrasonic applicator for causing ultrasonic beam energy to effect ultrasonic scanning of a body region along successive scanning lines, an image registering device with a line generator for controlling the imaging of echo impulses along an image line and with an image generator for controlling image line displacement of successive image lines to form an image during displacement of the ultrasonic beam energy for scanning along successive scanning lines of the body region, said ultrasonic applicator comprising a parabolic reflector and ultrasonic transducer means operable for the transducing of ultrasonic beam energy relative to the successive scanning lines via successive points along border zones and along an intervening central zone of the parabolic reflector during rotation of the transducer means about the focal line of said reflector, and angle responsive signal generator means responsive to the angular movement of the ultrasonic transducer means and operable for controlling the image generator to produce image line displacement at a more rapid rate during transducing of ultrasonic beam energy via points at the border zones of the reflector and at a relatively slower rate during transducing of ultrasonic beam energy via points in the central zone of the reflector, wherein the improvement comprises said angle responsive signal generator means including rotary mark carrier means having a succession of angularly offset marks, and rotatable in synchronism with the rotation of the ultrasonic transducer means, and mark scanner means operably associated with the marks of said mark carrier means for generating mark signals in response to the scanning of the successive marks during rotation of said mark carrier means, the marks of said rotary mark carrier means having a variable spacing such that the mark scanner means scans a relatively rapid succession of marks during transducing of the ultrasonic transducer means via points in the border zones of the reflector and scans a relatively less rapid succession of marks during transducing via points in the central zone of the reflector, and said mark scanner means being operatively connected to said image generator for controlling the rate of image line displacement in accordance with the rate of scanning of said marks by said mark scanner means.

2. Ultrasonic imaging apparatus in accordance with claim 1 with said mark scanner means producing electrical pulses in dependence upon the chronological succession of individually scanned marks, with said electrical pulses exhibiting a correspondingly shorter pulse interval during scaning of a rapid succession of marks than during scanning of a less rapid succession of marks.

3. Ultrasonic imaging apparatus in accordance with claim 2, with said image generator comprising voltage generator means connected with said mark scanner means and responsive to the electrical pulses therefrom for generating an image line displacement voltage which has a relatively rapid rate of increase during scanning of a relatively rapid succession of marks and which has a relatively slower rate of increase during scanning of a less rapid succession of marks.

4. Ultrasonic imaging apparatus according to claim 3, with said voltage generator comprising a pulse counter connected with said mark scanner means for counting the electrical pulses in accordance with the successive marks scanned by sid mark scanner means, and a digital to analog converter controlled by said counter for producing an output voltage in proportion to the count registered by said counter and for producing a relatively rapidly increasing output voltage during scanning of relatively rapid succession of marks and for producing a less rapidly increasing output voltage during scaning of less rapidly occurring marks.

5. Ultrasonic imaging apparatus in accordance with claim 4, with said rotary mark carrier means having control means for determining the transmitting and receiving periods of the ultrasonic transducer means in each revolution thereof, and said mark scanner mans being responsive to said control means to reset said pulse counter to an initial value in preparation for a new image generating cycle.

6. Ultrasonic imaging apparatus according to claim 1, with said mark carrier means having control marks for determining the transmissing and receiving periods of said ultrasonic transducer means.

7. Ultrasonic imaging apparatus in accordance with claim 6, with said ultrasonic transducer means having a plurality of transducer units which are sequentially activated in each cycle of operation for the purpose of transmission and reception of ultrasonic energy, and said mark scanner means being responsive to said control marks to control the activation of the successive transducer units in each cycle of operation and to correspondingly control the image generator so as to form an image during the active interval of each of the transducer units.

8. Ultrasonic imaging apparatus in accordance with claim 1, with said ultrasonic transducer means having a plurality of transducer units for sequential activation in each cycle of operation, said mark carrier means having a first control mark means for determining the transmitting and receiving periods of the respective transducer units and having a further control mark operable together with the control mark means for the purpose of determining the initiation of the operating cycle of the transducer mans, said mark scanner means being responsive to the scanning of the further control mark in conjunction with the control mark means to effect the activation of predetermined one of said transducer units.

9. Ultrasonic imaging apparatus in accordance with claim 8, with said mark carrier means having a plurality of control marks with angular separation corresponding to the angular separation of said transducer units and having a further control mark coordinated with one only of said plurality of control marks such that the mark scanner means respond to the one of said control marks and said further control marks each time the one of said transducer units begins a traverse of the parabolic reflector.

10. Ultrasonic imaging apparatus in accordance with claim 9, with transducer switching means controlling the sequential activation of the transducer units and comprisinga ring counter controlled by the mark scanner means and responsive to the scanning by the mark scanner means of the further control mark to reset to an initial condition, and being responsive to the successive scanning of the control marks by the mark scanner means to step to successive counting conditions so as to activate the respective transducer units in sequence as the respective transducer units begin traverse of the parabolic reflector.

11. Apparatus according to claim 1 with impulse rate control means operatively connected with said ultrasonic transducer means for controlling the rate of production of impulses of ultrasonic beam energy during rotation of said transducer means, and operatively connected with said mark scanner means and responsive to the rate of mark scanning thereby to vary the rate of production of impulses of ultrasonic beam energy in accordance with the rate of mark scanning by said mark scanner means.

12. Apparatus according to claim 11 with said impulse rate control means being operatively connected with said mark scanner means for synchronizing the production of impulses of ultrasonic beam energy with the instantaneous rate of mark scanning by said mark scanner means.

13. Apparatus according to claim 1 with said ultrasonic transducer means having impulse rate control means responsive to a modulating signal to vary the rate of production of impulses of ultrasonic beam energy in accordance with said modulating signal, and circuit means interposed between said mark scanner means and said impulse rate control means and responsive to the rate of mark scanning of the mark scanner means to generate a scanner rate responsive voltage ($U_4$) which rises at a rate proportional to the instantaneous mark scanner rate during each scanning cycle and then returns to an initial value and differentiating means (54) for receiving said scanner($U_5$) to said impulse rate control means in each scanning cycle which has a relatively higher value at the beginning and end of each cycle and a relatively lower value at the mid part of the cycle.

14. Apparatus according to claim 1 with said mark carrier means comprising a mark carrier having an annular section of translucent material rotatable with the ultrasonic transducer means and having opaque lines disposed at varying angular intervals along said annular section, and said mark scanner means comprising an optoelectric system for establishing light transmission through the annular section which is interrupted by each of said opaque lines to generate an electrical mark signal.

* * * * *